United States Patent
Bova

(10) Patent No.: US 6,661,872 B2
(45) Date of Patent: Dec. 9, 2003

(54) INTENSITY MODULATED RADIATION THERAPY PLANNING SYSTEM

(75) Inventor: Frank J. Bova, Gainesville, FL (US)

(73) Assignee: University of Florida, Gainesville, FL (US)

( * ) Notice: Subject to any disclaimer, the term of this patent is extended or adjusted under 35 U.S.C. 154(b) by 118 days.

(21) Appl. No.: 10/015,891

(22) Filed: Dec. 17, 2001

(65) Prior Publication Data

US 2003/0086528 A1 May 8, 2003

Related U.S. Application Data

(60) Provisional application No. 60/255,389, filed on Dec. 15, 2000.

(51) Int. Cl.$^7$ ................................................. A61N 5/10
(52) U.S. Cl. ......................................... 378/65; 378/901
(58) Field of Search .................................. 378/65, 901

(56) References Cited

U.S. PATENT DOCUMENTS

| | | | |
|---|---|---|---|
| 5,622,174 A | 4/1997 | Yamazaki | 128/661.09 |
| 5,663,999 A | 9/1997 | Siochi | 378/65 |
| 5,669,387 A | 9/1997 | Mine | 128/661.09 |
| 5,673,700 A | 10/1997 | Yamazaki et al. | 128/661.09 |
| 5,701,897 A | 12/1997 | Sano | 128/661.09 |
| 5,764,723 A | 6/1998 | Weinberger et al. | 378/65 |
| 6,038,283 A | 3/2000 | Carol et al. | 378/65 |
| 6,052,435 A | 4/2000 | Hernandez-Guerra et al. | 378/150 |
| 6,076,005 A | 6/2000 | Sontag et al. | 600/413 |
| 6,142,925 A | 11/2000 | Siochi et al. | 600/1 |
| 6,504,899 B2 * | 1/2003 | Pugachev et al. | 378/65 |

* cited by examiner

*Primary Examiner*—Edward J. Glick
*Assistant Examiner*—Jurie Yun
(74) *Attorney, Agent, or Firm*—Miles & Stockbridge, P.C.; Dennis P. Clarke

(57) ABSTRACT

A method for planning an intensity modulated radiation therapy system comprising outlining a 3D target volume, providing relative radiation intensities of the 3D, a) selecting specific beam directions for the system to use and b) optimizing the system using an arcing paradigm; back-projecting the given intensities to the selected beam entry portals; sub-dividing each entry portal into discrete dose elements; applying thereto a cost function that scores the goodness of the plan by positively rewarding doses in selected regions and negatively rewarding doses in protected regions, and adjusting the weights of each of the dose elements to increase the overall score.

1 Claim, No Drawings

INTENSITY MODULATED RADIATION THERAPY PLANNING SYSTEM

This application claims the benefit of provisional application No. 60/255,389 filed Dec. 15, 2000.

BACKGROUND OF THE INVENTION

1. Field of the Invention

The present invention relates to a system for optimally planning an Intensity Modulated Radiation Therapy system.

2. Description of the Prior Art

So-called Intensity Modulated Radiation Therapy (IMRT) systems are well known in the art [see U.S. Pat. Nos. 5,663,999; 6,142,925; 6,076,005; 6052,435; 6,038,283; 5,764,723; 5,701,897; 5,673,700; 5,669,387; 5,622,174, and "Intensity Modulated Radiation Therapy—Complications," Advance for Administrators in Radiology, Radiology Technology Profile, July, 1996]. IMRT systems using Dynamic Multileaf Collimators (DMLC) entail rotation of the linear accelerator gantry in coordination with the opening and closing of the DMLC jaws. When delivering IMRT, at any desired combination of gantry angle and DMLC jaw position, it is necessary that the linear accelerator beams be properly gated to insure that radiation is only applied at the proper time and in the proper doses.

The field of radiation delivery has long relied upon dose delivery using either uniform fields or fields that are have a dose gradient in only one direction. These latter fields are commonly known as "wedged fields". Intensity Modulated Radiation Therapy systems demand that treatment planners be provided with a tool that allows optimization dose distributions. Up until the present time such planning has been either extremely difficult to design when using routine planning techniques or else simply impossible. While one of the initial proposals of IMRT planning advocated a simple method of involving the packing of the planned target volume with spheres of dose, each having a unique intensity, this technique was never fully developed. Other techniques based upon back projections and iterative optimization techniques have been advanced and commercialized. Although these techniques have been applied to routine radiation therapy targets and even to some radiosurgery targets they have yet to produce the highly conformal dose distributions with high dose gradients that are the hallmark of a good radiosurgery treatment plan.

SUMMARY OF THE INVENTION

The inventors have been active in the field of radiosurgery for approximately 15 years. During this time approximately 1800 radiosurgery patients have been treated thereby. This has provided the inventors with extensive experience in the planning and optimization of radiosurgery dose distributions. In order to assist those who are new to the treatment technique of developing high quality radiosurgery treatment plans, i.e. radiation dose distributions that are 1) highly conformal and 2) have exceedingly high dose gradients, the present invention provides a rule based system for dose planning. The system of the invention allows the clinician to use routine target outline techniques to define the 3D target volume and then the new computer code provides the location and intensity of the various "isocenters" used to "pack the 3D volume".

DETAILED DESCRIPTION OF THE INVENTION

The conformality of the final dose distribution provided by the system of the invention code is very similar to that produced by an expert human planner. The code relies upon a system to select a starting point for the optimization of each isocenter based upon a known "grass fire" algorithm that is applied to a user supplied 3D target outline. Using this starting point the system suggest an isocenter position and a collimator size. Using dose evaluation tools the user accepts or modifies that initial isocenter. The code then removes all of the 3D target volume covered by that isocenter and the algorithm reapplies the "grass fire" technique to the remaining 3D target volume, extracting the next isocenter. Then using the spacing and weighting tools available in the existing radiosurgery planning code the user can optimize the position and intensity of the second isocenter. This process is repeated until the appropriate percentage of the target outline is covered. The end result of this approach is the production of a treatment plan consisting of spheres of known position and known intensity, resulting in a plan that provides conformal coverage of the entire 3D target volume with vary rapid dose fall-off from the edge of the target volume.

Routine Intensity Modulated Radiation Therapy, IMRT, systems and practitioners have traditionally taken a very different path towards the design of the modulated radiation fields that provide conformal coverage of a 3D target volume. The process typically begins, in a manner similar to that described for automated sphere packing algorithms, i.e., with the outline of the 3D target volume. From there, however, the approach has been very different. The planner provides the system with the relative radiation intensities of the 3D regions, including target and normal tissues. The system then begins the automated optimization process. Usually the planner either, 1) selects specific beam directions for the system to use or, 2) allows the system to optimize using an arcing paradigm. In either case the next stage of optimization usually involves the back projection of the given intensities to the selected beam entry portals. Each entry portal is subdivided into discrete dose elements, usually 1 mm×1 mm to 10 mm×10 mm depending upon the algorithm and the supporting hardware. A cost function that scores the goodness of the plan, positively rewards doses in selected regions and negatively rewards doses in protected regions, is then evaluated. The system adjusts the weights, intensities, of each of the beam's intensity dose elements in an attempt to increase the overall score. The end result of this algorithm is a beam of varying intensities that when mapped back onto the patient's anatomy will achieve the requested dose plan.

For IMIRT, as applied to radiation therapies, the normal beam are anywhere from 5×5×5 cm (125 cc) to 20×20×20 cm (8,000 cc). For radiosurgery the normal beam sizes are 10 mm diameter (0.5 cc) to 30 mm diameter (14 cc). As can be seen the target volumes for radiosurgery are more than an order of magnitude smaller than those for routine radiotherapy. This volume difference results in problems maintaining the desired conformality and dose gradient when trying to apply routine radiotherapy IMIRT algorithms and hardware approaches to radiosurgery sized targets. The solution to the IMIRT problem for radiosurgery can be perceived as a re-formatting of the above mentioned sphere packing solution. It can be shown that while routine linac based radiosurgery plans are generated using an arcing paradigm, a nearly equivalent plan, one that employs a set number of fixed beams, can be substituted for each arc. The results of the fixed beam dose plan can be very similar to that provided by the arcing plan. For example, a typical set of arc plan for each individual isocenter may be comprised of 5 arcs each extending over 100 degrees of arc span. Suppose that for each arc a fixed beam is placed at the beginning, middle and end of that arc along the same entrance plane in the patient, i.e. at that specific table angle. These three beams would produce a dose distribution very close to that of the individual arc. If this is done for each arc in that set of 5 arcs, a set of 15 fixed beams results. This set of fixed beams can be substituted for the arcing beam set.

While the many beams contained in the routine radiosurgery are set distribute the entrance and exit beams effectively, increased reduction of dose to critical structures can be achieved by ensuring that individual beam paths avoid traversing each critical structure. It is also advantageous to produce dose distributions that closely approximately a spherical distribution. To accomplish this latter goal set of isotropically spaced beams have been developed. These sets vary in the number of beams they contain. Sets containing anywhere from 3 to 9 beams have appeared in the literature. These isotropic sets have extended to include up to 21 beams. The number of beams, the size of the spherical dose distribution and the available number of degrees available for beam placement all interact to produce an optimum set of beams for a specific clinical target. Once the optimum number of beams has been decided upon the beam set, sometimes termed a beam bouquet, can be rotated about the target to optimize the dose to the target and minimize the dose to critical structures. This is achieved by producing a score function which rewards the beams that intersect the most target volume while giving a penalty to beams which deposit dose in a critical structure. The bean bouquet is rotated bout the target until this function is optimized providing for the most target coverage and the minimum dose to critical structures. This beams set can then be used as the set to plan the sphere packing for a specific clinical target structure.

When multiple isocenter plans are developed it is usual for each of these arcing sets to use the same circular collimator. The relative intensity of each fixed circular beam portal must also be provided and can be arrived at in one of two ways. The sphere packing plan provides the relative intensity of each individual arc. The intensity derived from a sphere packing algorithm can be remapped onto the corresponding set of fixed beams that are positioned to approximate that specific arc. While this is an approximation it provides an excellent estimate of the dose map that would be required by the fixed beam set to mimic the arcing dose plan. An alternative method is to create a set of fixed beams that would be used by the dose-planning program in place of the arcing plan. In this latter technique the intensity of each individual arc would be precisely computed thus avoiding any errors involved in mapping the arcing plan to the fixed beam plan.

The above approach has several advantages to the more routine IMRT approach currently used in radiation therapy. First, through the use of circular beams, employing beams as small as 5 mm diameter, the intensity map is generated on a much finer matrix then can usually be handled by an IMRT algorithm. The use of a 1×1×1 mm matrix, for planning and delivery, in a routine IMIRT system would increase the number of dose elements to be evaluated by several orders of magnitude. The arcing paradigm allows the planning system to only address the dose elements contained within the individual beam being optimized. This approach significantly simplifies the IMRT optimization computations. In effect it segments the computation allowing for smaller portions of the target to be individually optimized.

Secondly, the smaller spherical beam allows the system to achieve very high spatial resolution, providing high spatial fidelity, over the target's surface. While this spatial resolution may be unnecessary in routine IMRT, the size and shape of radiosurgery targets mandate that conformal plans have significantly higher spatial frequencies.

Thirdly, after an optimized plan has been designed, the use of fixed beams allows for the grouping of beams of similar table and gantry positions into composite intensity modulated beams. If for example the 15-fixed beam set used, as in the above example, no matter how complex the plan is, it could be simplified into 15-fixed intensity modulated beams. This can significantly reduce the treatment times when compared to those required when multiple isocenters and an arcing paradigm are used.

The above system can be extended to routine radiotherapy IMRT planning. A routine radiation therapy planning system can apply this technique, allowing larger circular beams to be applied, and then casting them into fixed beam portals. It can also use fewer fixed beams if the constraints on dose gradient can be relaxed. In either the radiosurgery case or the routine radiotherapy case the plans which result from the above described system can be executed through use of either a multileaf collimator, MLC, or a mini or micro multileaf collimator, mMLC. The MILC or mMLC can be used to approximate the individual circular beam, applying the beams as if circular collimators were used. In another mode the composite dose map from all collimators at a set gantry angle can be created and delivered though any number of techniques including, for example, "point and shoot" or "sliding vein". The dose could also be applied through a system of interchangeable circular collimators.

What is claimed is:

1. A method for planning an intensity modulated radiation therapy system comprising outlining a 3D target volume, providing relative radiation intensities of the 3D regions, including target and normal tissues, a) selecting specific beam directions for the system to use and b) optimizing the system using an arcing paradigm; back-projecting the given intensities to the selected beam entry portals; sub-dividing each entry portal into discrete dose elements; applying thereto a cost function that scores the goodness of the plan by positively rewarding doses in selected regions and negatively rewarding doses in protected regions, and adjusting the weights of each of the dose elements to increase the overall score.

* * * * *